United States Patent
Kitchen et al.

(10) Patent No.: US 6,258,978 B1
(45) Date of Patent: Jul. 10, 2001

(54) CONTROLLING PRODUCT STREAM OXYGEN CONTENT IN PROCESS FOR THE PRODUCTION OF VINYL ACETATE

(75) Inventors: Simon James Kitchen, Hillam; Alasdair Iain Thomson, Elloughton; Bruce Leo Williams, Elloughton Brough, all of (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/434,180

(22) Filed: Nov. 5, 1999

(30) Foreign Application Priority Data

Dec. 4, 1998 (GB) .................................................. 9826754

(51) Int. Cl.$^7$ ............................ C07C 67/55; C07C 69/15
(52) U.S. Cl. ........................................... 560/248; 560/261
(58) Field of Search ...................... 560/218, 248, 560/261

(56) References Cited

U.S. PATENT DOCUMENTS 5,550,281  8/1996  Cirjak et al. .

FOREIGN PATENT DOCUMENTS

| 0 685 449 A1 | 12/1995 | (EP) . |
| 0 845 453 A2 | 6/1998 | (EP) . |
| 0 847 982 | 6/1998 | (EP) . |

*Primary Examiner*—Paul J. Killos
*Assistant Examiner*—Robert W. Deemie
(74) *Attorney, Agent, or Firm*—Nixon & Vanderhye

(57) ABSTRACT

In a process for the production of vinyl acetate by reacting ethylene, acetic acid and an oxygen-containing gas in a reactor to produce a process stream which is removed from the reactor as an outlet stream, the process is improved by maintaining the oxygen concentration of the outlet stream at or near its flammability limit.

20 Claims, 1 Drawing Sheet

Figure 1:
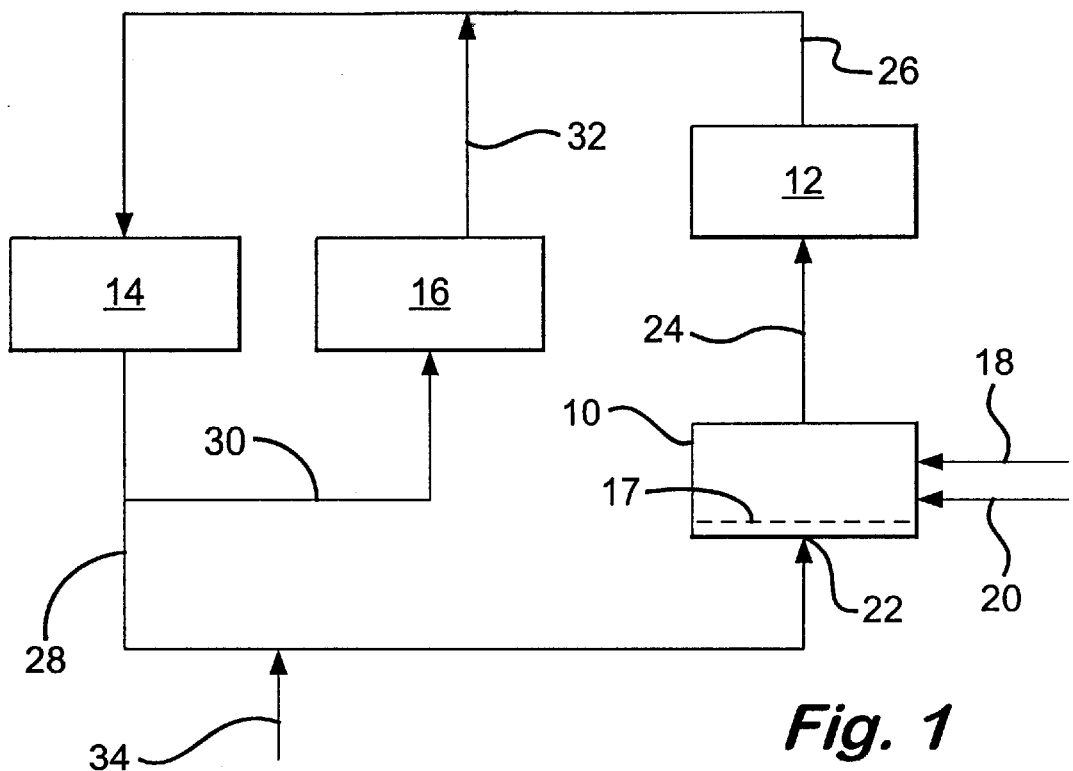

CONTROLLING PRODUCT STREAM OXYGEN CONTENT IN PROCESS FOR THE PRODUCTION OF VINYL ACETATE

The present invention relates to a process for the production of vinyl acetate.

Vinyl acetate may be produced by the acetoxylation of ethylene. In a typical vinyl acetate production process, ethylene, acetic acid and oxygen are introduced into a reactor via an inlet. The reactants are contacted with a palladium-containing catalyst and react to produce an outlet stream which is removed from the reactor and cooled. Vinyl acetate, water and the unreacted acetic acid in the outlet stream are condensed and separated for further purification. The remaining gaseous components of the outlet stream (e.g. ethylene) are compressed and recycled.

The rate of acetoxylation increases as the concentration of oxygen in the reactor is increased. However, the amount of oxygen that may be introduced into the reactor is limited by the flammability limit of the reactant mixture. The flammability limit is defined as the highest concentration of oxygen in a mixture that will fail to sustain combustion. If the oxygen concentration exceeds this flammability limit, a fire or explosion could result.

Various steps have been taken to minimise the risk of such a fire or explosion. For example, in the fixed-bed reactor of EP 0 845 453, the concentration of oxygen in the inlet gas composition is closely monitored and maintained at or near a threshold value. The mathematical approximations used to define this threshold value are described in EP 0 845 453 which is incorporated herein by reference. When the inlet oxygen concentration exceeds this threshold value, a shut-down signal is activated, and the reaction is quenched by shutting off the ingress of fresh oxygen into the reactor.

A problem with this arrangement is that the oxygen concentration in the reactor is limited by the flammability limit of the feed mixture in the inlet, rather than the flammability limit of the reaction mixture in the reactor itself. In general, a higher concentration of oxygen may be tolerated in the latter and, accordingly, the shut-down signal may be activated too soon before the concentration of oxygen in the reactor reaches an optimum value.

The problem may be avoided in a fluid bed reactor by introducing fresh oxygen via a separate inlet as described in U.S. Pat. No. 5 550 281. This arrangement, however, is unsuitable for fixed bed systems.

We have now developed a process for producing vinyl acetate in which the concentration of oxygen in the reactor is not limited by the amount of fresh oxygen that is introduced into the reactor via an inlet. This process is applicable to both fixed bed and fluid bed reactors.

According to the present invention, there is provided a process for the production of vinyl acetate, said process comprising the steps of:

(a) introducing ethylene, acetic acid and an oxygen-containing gas into a reactor, (b) reacting said ethylene, acetic acid, and oxygen-containing gas in the presence of an acetoxylation catalyst in said reactor to produce a process stream, (c) removing said process stream from the reactor as an outlet stream, and maintaining the oxygen concentration of said outlet stream at or near its flammability limit.

The present invention has the advantage that by maintaining the concentration of oxygen in the outlet stream at or near its flammability limit, an increase in the productivity and selectivity of the vinyl acetate production process is observed.

As explained above, the flammability limit of a mixture is defined as the highest concentration of oxygen in the mixture that will fail to sustain combustion. This limit may be expressed as a function of pressure, temperature and the composition of the mixture, as described by the empirical equations disclosed in EP 0 845 453.

In this application, the term "outlet stream" is taken to encompass the initial stream emerging directly from the reactor and any stream subsequently derived from the initial stream, except for the stream entering the reactor at its inlet. For example, after leaving the reactor, the outlet stream may be returned to the reactor via a recycle loop involving one or more processing stages. In one processing stage, the outlet stream emerging from the reactor may be introduced into a separation unit where liquid components of the outlet stream such as vinyl acetate, water and/or unreacted acetic acid are removed. The separation unit may take the form of one or more distillation columns.

In a further processing stage, some or all of the outlet stream leaving the separation unit may be introduced into a compressor. Some of the outlet stream leaving the separation unit may then be introduced into a carbon dioxide removal unit. Here, some or all of the carbon dioxide in the outlet stream is removed. The outlet stream is then re-directed into the compressor to complete the recycle loop.

The composition of the outlet stream varies at different points along the recycle loop. For example, the composition of the outlet stream emerging from the reactor may be different to the composition of the outlet stream emerging from each of the various processing stages of the recycle loop.

Together with changes in temperature and pressure, these differences in composition may cause the flammability limits of the outlet stream to vary at different points along the recycle loop. For example, in one embodiment, the flammability limit of the outlet stream between the reactor and separator unit is different to the flammability limit of the outlet stream between the separator unit and the compressor. The flammability limit of the outlet stream may also change after compression and, subsequently, after carbon dioxide has been removed. To avoid the risk of fire/explosion, the oxygen concentration of the outlet stream should be maintained at or below the flammability limit at all points along the recycle loop.

The flammability limit in the outlet stream may be up to and including 10 vol. % oxygen, for example 7 vol. % oxygen. Suitably, the oxygen concentration in the outlet stream is maintained at or below 10 vol. % oxygen.

The process of the present invention may further comprise the step of shutting down the reactor in the event that the concentration of oxygen in the outlet stream exceeds or is likely to exceed its flammability limit. To determine whether shut-down is necessary, the oxygen concentration of the outlet stream is monitored, for example, by computer at various points along the recycle loop. For example, in one embodiment, the oxygen concentration of the outlet stream is monitored at four stages along the recycle loop. Firstly, as the outlet stream emerges from the reactor; secondly, as it emerges from the separation unit; thirdly, as it emerges from the compressor and fourthly, as it emerges from the carbon dioxide removal unit. When the oxygen concentration at any one of these stages exceeds a threshold value defined by the flammability limit, the shut-down signal is activated.

In an alternative embodiment, the oxygen concentration of the outlet stream is monitored at a single stage or "trip point". When the oxygen concentration at this trip point exceeds a threshold value defined by the flammability limit, the shut-down signal is activated. In theory, the trip point may be defined as the point along the recycle loop at which the outlet stream is at or closest to its flammability limit. In practice, however, fluctuations in temperature, pressure and outlet stream composition may cause the outlet stream to exceed its flammability limit other than at the trip point. This has to be taken into account when calculating the threshold oxygen concentration at the trip point. The threshold value may be defined by a flammability equation such as described in EP-A-0845453 (incorporated herein by reference) with allowance for errors (for example 95% confidence limit), for residence time in the sampling, for trip system response time, for equipment accuracy and for natural variations in the plant operation.

The threshold value may suitable be set at or below 10 vol. % oxygen. For example, with a flammability limit of 7 vol. % the threshold value may be set at 4.0 vol. % oxygen, although other values may be used depending upon the factors herein before described.

In one embodiment, the outlet stream is monitored at a point between the reactor and the separator unit and a suitable threshold value at this point is 4.0 vol. % oxygen. In other embodiments, the outlet stream is monitored at other points along the recycle loop, for example, as it emerges from the separator unit and/or the carbon dioxide removal unit.

The oxygen concentration at the trip point may be monitored using an oxygen analyser. For example, the oxygen concentration may be monitored by using an analyser which measures the paramagnetism of the outlet stream as it emerges from the separator unit and/or carbon dioxide removal unit. Such analysers (e.g. SERVOMEX) comprise components which tend to be adversely affected by condensable vapours, high temperatures and pressures. Accordingly, these analysers cannot be used where high temperature and pressure conditions are encountered, for example, adjacent the reactor exit. Thus, to analyse the outlet stream as it emerges from the reactor exit, the stream has to be pre-treated, for example, by cooling the stream to remove the condensable vapours, and de-pressurising.

The oxygen concentration of the outlet stream as it emerges from the reactor may be monitored by wavelength scanning using a monochromatic light source. The technique is carried out preferably in the near infra red (NIR), although other wavelengths may be used (a suitable wavelength in the near infra red is approximately 700 to 1000 nm, preferably, approximately 760 nm, that is ±5 nm) using an apparatus comprising a transmitting diode laser and a detector. A suitable apparatus is manufactured under the trade mark LaserGas by Norsk Electro Optikk A/S (Norway).

Diode laser spectroscopy is based on the selection of one single absorption line, preferably in the NIR spectral range for oxygen gas. Care has to be taken to ensure that no other gases have absorption lines at the chosen wavelength. The frequency of the diode laser is tuned to correspond to the single absorption line for oxygen by adjusting the temperature and driving current of the laser. The spectral width of the diode laser is considerably narrower than the spectral width of the absorption line for oxygen. By varying the diode laser current, the diode laser wavelength is scanned across the absorption line.

The oxygen molecules in the optical path between the diode laser and the detector absorb the transmitted laser light, causing the intensity of the detected laser to vary as a function of wavelength. Thus, the detected shape and size of the absorption line may be used to calculate the amount of oxygen between the transmitter and the receiver.

LaserGas™ analysers will tolerate temperatures as high as 1000° C. and pressures of up to 20 bar. The oxygen concentration of the gas inside the reactor may thus be monitored. It is important that acetic acid and other condensable components in the gas stream not be allowed to condense on the windows of the detector. To achieve this the windows may purged with a gas which does not interfere with the absorption spectrum. A suitable path length should be chosen, typically 1 metre, to ensure adequate detector sensitivity. This may be achieved by placing the analyser across a vessel or large pipework/ductwork. Alternatively, this may also be achieved by feeding the gas to be monitored into the longitudinal centre of a tube having purge gases fed intermediate the monitored gas feed point and the ends of the tube, such that the gas in the centre of the tube comprises essentially the gas to be monitored and the purge gas streams exit at each end of the tube. The windows of the detector are then mounted transverse to the tube in the centre, in the region comprising essentially the gas to be monitored. Suitably ethylene may be used as purge gas.

The process of the present invention may be carried out in a fixed bed or a fluid bed reactor. In a fixed bed reactor, a mixture of oxygen, acetic acid and ethylene is introduced into a fixed bed reactor via an inlet. In a fluid bed reactor, the oxygen, ethylene and acetic acid are generally introduced separately. This eliminates the risk of ethylene and/or acetic acid combusting prior to entry into the reactor. The reactants are then contacted with a fluidised catalyst material which is continuously mixed with the reactants to form a homogenous mixture. This allows the acetoxylation reaction to occur under isothermal conditions, whereby the heat generated by the oxacetylation reaction is evenly distributed throughout the reactor. This reduces the risk of explosion and/or fire occurring within the reactor. Thus, the amount of oxygen that may be employed in a fluid bed reactor is not constrained by the flammability limit of the sum of the reactant feed components, if at least part of the oxygen is fed to the reactor separately to the other feed components.

In both fluid bed and fixed bed reactors, the reaction conditions are controlled to ensure that the oxygen concentration in the outlet stream is maintained at or near a maximum value. This may be achieved by controlling the rate of oxygen conversion in the reactor, which in turn is dependant on a number of factors, for example, the nature of the catalyst, the reaction temperature, reactor size and feed throughput.

The catalyst of the present invention may comprise a Group VIII metal such as platinum and/or palladium. Preferably, palladium is employed. The metal may be present in a concentration of greater than 0.2% by weight, preferably greater than 0.5% by weight, especially greater than 1% by weight based upon total weight of catalyst. The metal concentration may be as high as 10% by weight. Suitable sources of palladium include palladium (II) chloride, $Na_2PdCl_4$, $K_2PdCl_4$, $H_2PdCl_4$, palladium acetate, palladium (II) nitrate and/or palladium (II) sulphate.

In addition to a Group VIII metal, the catalyst may comprise a promoter. Suitable promoters include gold, copper and/or nickel. A preferred promoter is gold. Suitable sources of gold include gold chloride, tetrachloroauric acid ($HAuCl_4$), $NaAuCl_4$, $KAuCl_4$, dimethyl gold acetate, barium acetoaurate or gold acetate, with $HAuCl_4$ being preferred. The promoter metal may be present in an amount of from 0.1 to 10% by weight in the finished catalyst.

Preferably, the catalyst composition also comprises a co-promoter material. Suitable co-promoters include Group I, Group II, lanthanide or transition metals, for example copper, cadmium, barium, potassium, sodium, iron, manganese, nickel, antimony, and/or lanthanum, which are present in the finished catalyst as salts, e.g. an acetate salt. The preferred salts are potassium or sodium acetate. The co-promoter may be present in the catalyst composition in a concentration of up to 15%. Where the catalyst is a fixed bed catalyst, the co-promoter concentration is preferably between 3 and 11 wt %. Where the catalyst is a fluid bed catalyst, the co-promotor may be present in a concentration of up to 11 wt %, preferably 3 to 6 wt %, of the total catalyst.

The catalyst material may be supported. Suitable catalyst supports include porous silica, alumina, silica/alumina, silica/titania, titania, zirconia or carbon. Preferably the support is silica. Suitably, the support may have a pore volume from 0.2 to 3.5 mL per gram of support, a surface area of 5 to 800 $m^2$ per gram of support and an apparent bulk density of 0.3 to 1.5 g.mL. The support for a fluid bed catalyst may typically have a particle size distribution such that at least 60% of the catalyst particles have a particle diameter of below 200 microns preferably at least 50% less than 105 microns and no more than 40% of the catalyst particles have a diameter of less than 40 microns.

The catalyst may be prepared by any suitable method. For example, the first stage of the catalyst preparation process may involve impregnation of the support material with a solution containing the required Group VIII metal and the promoter metal in the form of soluble salts. Examples of such salts are soluble halide derivatives. The impregnating solution is preferably an aqueous solution and the volume of solution used is such that it corresponds to between 50 and 100% of the pore volume of the support, preferably 50 to 99% of the pore volume.

The impregnated support is dried at ambient or reduced pressure and from ambient temperature to 150° C., preferably 60 to 120° C. prior to metals reduction. To convert such materials into the metallic state, the impregnated support is treated with a reducing agent such as ethylene, hydrazine or, formaldehyde or hydrogen. If hydrogen is used, it will usually be necessary to heat the catalyst to 100 to 850° C. in order to effect complete reduction.

After the steps described above have been carried out, the reduced catalyst is washed with water and then dried. The dried carrier is then impregnated with the required amount of co-promoter and thereafter dried.

The method of catalyst preparation may be varied to optimise catalyst performance based on maximising vinyl acetate yield and selectivity.

The activity of the catalyst may decrease with time. This may arise as the concentration of volatile co-promoter in the catalyst decreases with use. To maintain a constant concentration of co-promoter in the catalyst, fresh co-promoter may be added to the catalyst during the reaction. This may suitably be carried out by adding the co-promoter material to the liquid acetic acid feed or to the liquid recycle acetic acid. Alternatively, the additional co-promoter may be introduced as a solution (e.g. in water or in acid) directly by spraying through a suitable injection means such as a nozzle. In a fluid bed reactor, catalyst material may be removed from the reactor and replaced with fresh catalyst so as to maintain the activity of the catalyst and the concentration of oxygen in the outlet/recycle stream at desirable levels.

The process is carried out in a reactor and may suitably be operated at a temperature of 100 to 400° C., preferably 140 to 210° C. and, most preferably, 140° to 190° C. The reaction may be carried out at a pressure of between 0.5 barg and 20 barg, preferably between 6 barg and 14 barg and, most preferably, between 7 barg and 12 barg.

The process of the present invention may be carried out in a reactor capable of holding 10 to 50 tonnes of fixed bed catalyst or 10 to 300 tonnes, preferably 30 to 150 tonnes, and especially 50 to 100 tonnes of fluid bed catalyst. The effect on reactor size on the acetoxylation reaction is discussed in European patent application number 97309554.0/ publication number EP-A-0847982, which is incorporated herein by reference.

The ethylene used in the present process may be in substantially pure form or admixed with one or more of nitrogen, methane, ethane, carbon dioxide and water in the form of steam or one or more of hydrogen, $C_3/C_4$ alkenes or alkanes.

The oxygen-containing gas may suitably be air or a gas richer or poorer in molecular oxygen than air. Suitably, the gas may be oxygen diluted with a suitable diluent, for example, nitrogen, argon or carbon dioxide. Preferably, the gas is oxygen. In a fluid bed reactor, at least part of the oxygen may be fed to the reactor separately to the other components so that the total amount of oxygen fed exceeds its flammability limit in the total feeds to the reactor.

The acetic acid may be introduced into the reactor as a liquid or a vapour. In a fixed bed reactor, substantially all the acetic acid is introduced as a vapour. In a fluid bed reactor, a mixture of acetic acid vapour and liquid may be employed, but liquid acetic acid is preferred.

Liquid acetic acid may be introduced into the fluid bed reactor by any suitable injection means, for example a nozzle which may be a gas-induced atomising nozzle or liquid-only spray-type nozzles. Additionally, recycled acetic acid may be introduced into the reactor. The re-cycled acetic acid may be pre-mixed with the crude acetic acid or may be introduced into the reactor using a separate injection means.

Figure 2:
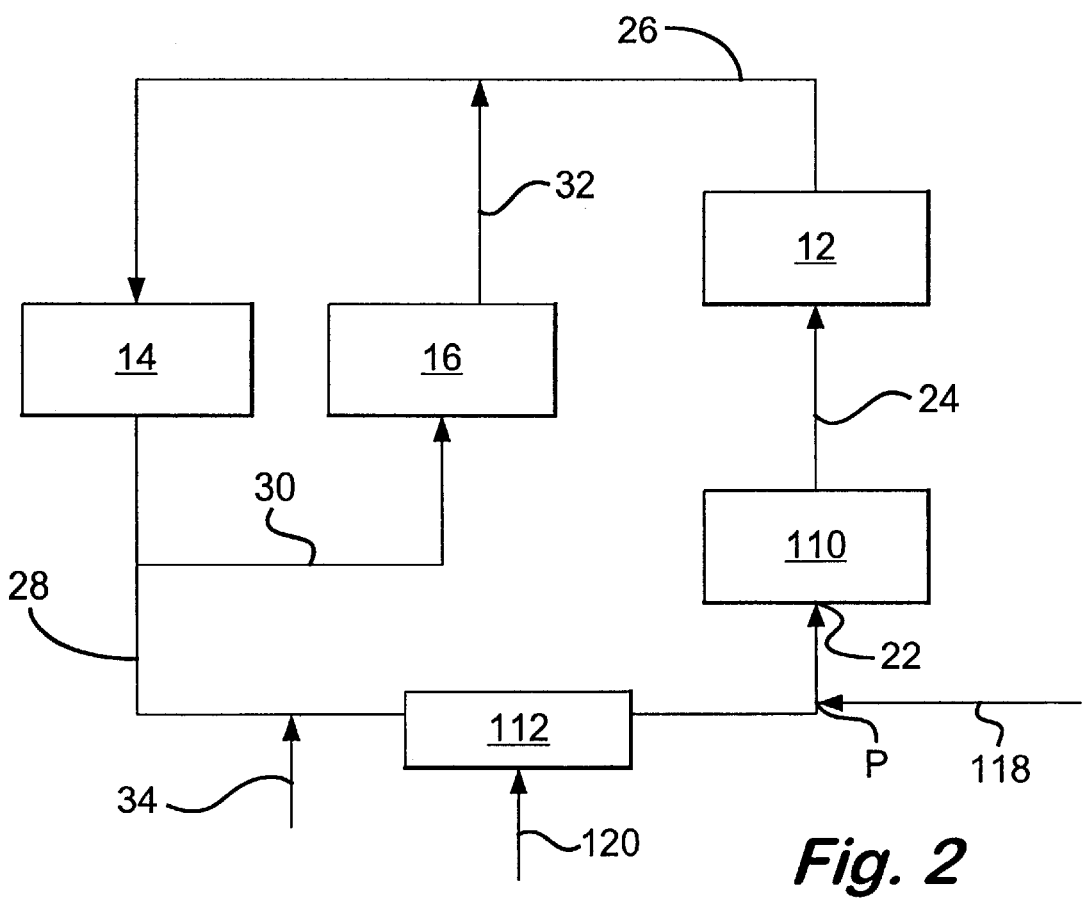

These and other aspects of the present invention will now be described, by way of illustration, with reference to the Examples and to the accompanying drawings in which:

FIG. 1 is a schematic illustration of a system for carrying out the process in accordance with a first embodiment of the present invention, and FIG. 2 is a schematic illustration of a system for carrying out the process in accordance with a second embodiment of the present invention.

FIG. 1 depicts a fluid bed system for carrying out a process in accordance with a first embodiment of the present invention. The system comprises a reactor 10, a separator unit 12, a compressor 14 and a carbon dioxide removal unit 16. The reactor 10 comprises two inlets 18, 20 for the introduction of oxygen and liquid acetic acid. The reactor 10 further comprises a grid 17. A mixture of fresh ethylene, and a recycle gas comprising unreacted oxygen and unreacted ethylene is introduced into the reactor 10 through the grid plate 17 via a third inlet 22.

In operation, the reactor 10 is charged with a catalyst to form a fluid bed. The feeds are introduced into the reactor 10 and contacted with the catalyst to produce a stream comprising vinyl acetate, water, carbon dioxide and unreacted reactants. The stream is removed from the reactor 10, cooled and introduced into the separation unit 12 via line 24. The vinyl acetate, water and the unreacted acetic acid in the stream are condensed and separated for further purification, whilst the remaining gaseous components are introduced into the compressor 14 via line 26. Once compressed, the gaseous components are recycled to the reactor via line 28.

A portion of the stream in line 28 is introduced to a carbon dioxide removal unit 16 via line 30. The unit 16 removes some or all of the carbon dioxide and inert gas which may otherwise accumulate in the stream. Once treated, the stream passes through line 32 and into line 26 for recycling to the reactor 10.

The ethylene concentration entering the reactor 10 is kept at desired levels by introducing fresh ethylene into line 28 via line 34.

The process is carried out under conditions such that the concentration of oxygen in the stream of lines 24, 26, 28 and 32 are maintained at a threshold value below the flammability limit.

FIG. 2 depicts a fixed bed system for carrying out a process in accordance with a second embodiment of the present invention. The system of FIG. 2 employs a fixed bed reactor 110, rather than a fluid bed reactor 10. Generally, the system of FIG. 2 is similar to the system of FIG. 1, and like parts are indicated by like numerals. However, unlike the system of FIG. 1, oxygen and acetic acid are not introduced directly into the reactor 110. Instead, acetic acid is introduced into the reactor 110 as a vapour using a vaporiser 112. Liquid acetic acid is fed into the vaporiser 112 via line 120. A further difference is that oxygen is not fed directly into the reactor 110 but into the stream at point "P" via line 118.

EXAMPLES

In the following Examples, the following assumptions and definitions apply:

1. The principle reactions occurring the reactor are:

$C_2H_4 + CH_3COOH + 0.5O_2 \rightarrow CH_2=CHOOCCH_3 + H_2O$, and $C_2H_4 + 3O_2 \rightarrow 2CO_2 + 2H_2O$ 2. The ideal gas law applies.
3. Percentage oxygen conversion is defined as the total percentage of oxygen converted to give vinyl acetate and carbon dioxide products.
4. Ethylene selectivity is defined as the percentage number of moles of ethylene converted to vinyl acetate divided by the total number of moles of ethylene converted to vinyl acetate and carbon dioxide. In other words:

Selectivity = 100 × (VAM moles out) / (VAM moles out + ½CO$_2$ moles out)

5. The flammability limit of the mixture in the reactor is taken to be 10 vol % oxygen. The flammability limit in the outlet stream is taken as a typical value of 7 vol. % oxygen. The oxygen concentration is monitored along line 24 and the threshold oxygen concentration at which the shut-down signal is activated is 4 vol. %.

Comparative Example A

Vinyl acetate is produced using the system shown in FIG. 2. The reactor 110 is charged with an acetoxylation catalyst to form a fixed bed.

The reactor 110 is operated at 140 to 190° C., 6 to 12 barg, and at an oxygen conversion rate of 70%, and an ethylene selectivity of 90%. The concentration of oxygen entering the reactor 110 is maintained at the flammability limit of 10 vol % of the total feeds to the reactor.

The reactor conditions are controlled such that the amount of oxygen exiting the reactor 110 forms 3.1 vol. % of the total volume of gas exiting the reactor 110. This concentration of oxygen is significantly below the threshold value of line 24 (4.0 vol %). Accordingly, this comparative example does not fall within the scope of the present invention.

The composition of the outlet stream is calculated on the basis of the assumptions above and the results are shown in Table A below.

TABLE A

| Component | Total reactor feed volume % | Reactor Exit moles | Reactor exit volume % |
|---|---|---|---|
| oxygen | 10 | 3.0 | 3.1 |
| ethylene | 55 | 45.7 | 47.7 |
| carbon dioxide | 20 | 21.9 | 22.8 |
| acetic acid | 15 | 6.6 | 6.9 |
| vinyl acetate | 0 | 8.4 | 8.8 |
| water | 0 | 10.3 | 10.7 |
| total moles | 100 | 95.8 | |

EXAMPLE 1

In this Example, vinyl acetate is produced using the system shown in FIG. 1. The reactor 10 is charged with the catalyst to form a fluid bed. This allows the acetoxylation reaction to occur under isothermal conditions, whereby the heat generated by the acetoxylation reaction is evenly distributed throughout the reactor. This reduces the risk of explosion and/or fire occurring within the reactor. Thus, the concentration of oxygen that may be employed in a fluid bed reactor is not constrained by the flammability limit of the reaction mixture. Accordingly, the concentration of oxygen entering the reactor 10 is maintained above the flammability limit, at 12.7 vol % of the total feeds entering the reactor.

The reactor 10 is operated at the same temperature, pressure, oxygen conversion rate and ethylene selectivity as the reactor 110 of Comparative Example A. In the present Example, however, the oxygen concentration in line 24 is increased to its maximum value of 4.0 vol % by increasing the amount of oxygen entering the reactor 10.

The composition of the outlet stream of Example 1 is calculated on the basis of the assumptions above and the results are shown in Table 1 below.

TABLE 1

| Component | Total reactor feed volume % | Reactor Exit moles | Reactor exit volume % |
|---|---|---|---|
| oxygen | 12.7 | 3.8 | 4.0 |
| ethylene | 52.3 | 40.4 | 42.7 |
| carbon dioxide | 20 | 22.4 | 23.6 |
| acetic acid | 15 | 4.3 | 4.6 |
| vinyl acetate | 0 | 10.7 | 11.3 |
| water | 0 | 13.0 | 13.8 |
| total moles | 100 | 94.7 | |

A comparison of Table A and Table 1 shows that higher production rates of vinyl acetate are observed when the total concentration of oxygen exiting the reactor is maintained at the threshold value defined by the flammability limit, rather than below it.

Comparative Example B

The procedure of Example 1 is repeated except that the reactor 10 is operated at an oxygen conversion rate of 60%. The feed composition fed into the reactor is identical to the feed composition of Comparative Example A. As can be seen from Table 3 below, the rate of oxygen conversion employed is not sufficient to maintain the concentration of oxygen of line 24 at or below the threshold value of 4.0 vol %. Instead, the concentration of oxygen in line 24 is 4.1 vol %, 0.1 vol % above the threshold value.

TABLE B

| Component | Total reactor feed volume % | Reactor Exit moles | Reactor exit volume % |
|---|---|---|---|
| oxygen | 10 | 4.0 | 4.1 |
| ethylene | 55 | 45.7 | 48.8 |
| carbon dioxide | 20 | 21.6 | 22.4 |
| acetic acid | 15 | 7.8 | 8.1 |
| vinyl acetate | 0 | 7.2 | 7.5 |
| water | 0 | 8.8 | 9.1 |
| total moles | 100 | 94.7 | |

Example 2

In this Example, the procedure of Comparative Example B is repeated except that 2.5% of the catalyst is replaced with fresh catalyst defined as being twice as active as the deactivated catalyst of Comparative Example B. This increases the rate of oxygen conversion to 61.5%, thereby reducing the concentration of oxygen in line 24 to its threshold value (4.0%).

The composition of the output stream is calculated on the basis on the assumptions above in Table 4 below.

TABLE 4

| Component | Total reactor feed volume % | Reactor Exit moles | Reactor exit volume % |
|---|---|---|---|
| oxygen | 10 | 3.9 | 4.0 |
| ethylene | 55 | 46.8 | 48.6 |
| carbon dioxide | 20 | 21.6 | 22.5 |
| acetic acid | 15 | 7.6 | 7.9 |
| vinyl acetate | 0 | 7.4 | 7.7 |
| water | 0 | 9.0 | 9.4 |
| total moles | 100 | 94.7 | |

A comparison of the results of Comparative Example B and Example 2 shows that for a given feed composition higher production rates of vinyl acetate are observed when the oxygen concentration of the outlet stream is maintained at the flammability limit rather than above it.

We claim:

1. A process for the production of vinyl acetate, said process comprising the steps of:
   (a) introducing ethylene, acetic acid and an oxygen-containing gas into a reactor,
   (b) reacting said ethylene, acetic acid, and oxygen-containing gas in the presence of an acetoxylation catalyst in said reactor to produce a process stream,
   (c) removing said process stream from the reactor as an outlet stream, and maintaining the oxygen concentration of said outlet stream at or near its flammability limit.

2. A process as claimed in claim 1 wherein the outlet stream is returned to the reactor via a recycle loop comprising one or more processing stages.

3. A process as claimed in claim 2 wherein the recycle loop comprises a processing stage in which the outlet stream is introduced into a separation unit wherein liquid components of the outlet stream comprising vinyl acetate, water and/or unreacted acetic acid are removed.

4. A process as claimed in claim 3 wherein some or all of the outlet stream leaving the separation unit is introduced into a compressor.

5. A process as claimed in claim 3 wherein some of the outlet stream leaving the separation unit is introduced into a carbon dioxide removal unit.

6. A process as claimed in claim 1 wherein the oxygen concentration in the outlet stream is maintained at or below 10% by volume.

7. A process as claimed in claim 3 wherein the oxygen concentration in the outlet stream is maintained at or below 10% by volume.

8. A process as claimed in claim 2 wherein the oxygen concentration is monitored at one or more stages in the recycle loop and the reactor is shut down if the oxygen concentration at any one of the monitored stage exceeds a threshold value defined by the flammability limit of oxygen in the outlet stream.

9. A process as claimed in claim 8 wherein the threshold value is set at or below 10 vol. % oxygen.

10. A process as claimed in claim 3 wherein the oxygen concentration is monitored at one or more stages in the recycle loop and the reactor is shut down if the oxygen concentration at any one of the monitored stage exceeds a threshold value defined by the flammability limit of oxygen in the outlet stream and the threshold value is 4.0% by volume at the stage between the reactor and the separation unit.

11. A process as claimed in claim 1 wherein the reactor is a fluid bed reactor.

12. A process as claimed in claim 6 wherein the reactor is a fluid bed reactor.

13. A process as claimed in claim 9 wherein the reactor is a fluid bed reactor.

14. A process as claimed in claim 10 wherein the reactor is a fluid bed reactor.

15. A process as claimed in claim 13 wherein the oxygen concentration in the total feeds to the reactor exceeds the flammability limit thereof.

16. A process as claimed in claim 14 wherein the oxygen concentration in the total feeds to the reactor exceeds the flammability limit thereof.

17. A process as claimed in claim 1 wherein the oxygen concentration in the outlet stream is monitored by means comprising a tuneable diode laser.

18. A process as claimed in claim 8 wherein the oxygen concentration in the outlet stream is monitored by means comprising a tuneable diode laser.

19. A process as claimed in claim 17 wherein the tuneable diode laser is operated in the near infra red region.

20. A process as claimed in claim 18 wherein the tuneable diode laser is operated in the near infra red region.

* * * * *